United States Patent
Goldstein (10) Patent No.: US 6,862,478 B1
(45) Date of Patent: Mar. 1, 2005

(54) CONNECTOR TOP FOR IMPLANTABLE MEDICAL DEVICE

(75) Inventor: Sheldon E. Goldstein, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 431 days.

(21) Appl. No.: 10/172,488

(22) Filed: Jun. 14, 2002

(51) Int. Cl.⁷ .............................................. A61N 1/375
(52) U.S. Cl. ....................................................... 607/37
(58) Field of Search ............................ 607/37; 439/909

(56) References Cited

U.S. PATENT DOCUMENTS

| | | | |
|---|---|---|---|
| 4,934,366 A | 6/1990 | Truex et al. ................. | 128/419 |
| 5,012,807 A | 5/1991 | Stutz, Jr. ..................... | 128/419 |
| 5,076,270 A | 12/1991 | Stutz, Jr. ..................... | 128/419 |
| 5,336,246 A | 8/1994 | Dantanarayana ............. | 607/37 |
| 5,545,188 A | 8/1996 | Bradshaw et al. ............ | 607/37 |
| 5,899,930 A | 5/1999 | Flynn et al. .................. | 607/37 |
| 6,029,089 A | 2/2000 | Hawkins et al. .............. | 607/37 |

FOREIGN PATENT DOCUMENTS

| | | | |
|---|---|---|---|
| EP | 0448651 | 10/1991 | ............ A61N/1/36 |
| EP | 0484483 | 5/1992 | ............ A61N/1/36 |
| EP | 0732124 | 9/1996 | .......... A61N/1/375 |

*Primary Examiner*—Scott M. Getzow (57) ABSTRACT

A connector assembly includes a ring sub-assembly mounted on the housing of an implantable medical device with a passage for slidably receiving a proximal terminal of an electrical lead. The interior of the connector assembly is sealed when engaged with the electrical lead and has an annular shoulder in the passage facing away from the entrance. An electrical contact on the ring sub-assembly engages the electrical lead and an electrical conductor extends from that contact to exterior regions for electrical engagement with an external feed-through terminal of the housing. A tip sub-assembly having a tubular extremity extending to a terminal rim is fittingly received within the passage and extends to a terminal bore for slidably receiving a tip electrode of the electrical lead. An electrically conductive resilient member is received in the passage sandwiched between the annular shoulder and the terminal rim of the tubular extension and is electrically coupled to the electrical contact of the connector assembly.

38 Claims, 11 Drawing Sheets

FIG.20

CONNECTOR TOP FOR IMPLANTABLE MEDICAL DEVICE

FIELD OF THE INVENTION

The present invention relates to an electrical connector used with an implantable medical device, such as a pacemaker, for connecting an implantable electrical lead to the electrical circuits within a hermetically sealed housing of the medical device. More particularly, the present invention relates to a feedthrough/connector for use with a sealed implantable pacemaker that reduces the number of components previously required, simplifies the tooling required for fabricating the components, and facilitates the assembly process.

BACKGROUND OF THE INVENTION

Modern pacemakers monitor the activity of a heart and provide a stimulation pulse in the absence of normal heart activity. Such devices are relatively small, light-weight and implantable. In order to sense and stimulate the heart, however, such pacemakers must be used with a pacemaker lead—an electrical conductor that carries electrical signals between the heart and the pacemaker. Advantageously, the pacemaker lead can be inserted into the heart transvenously through a relatively simple and well-known surgical procedure. Disadvantageously, one end of the lead (designated herein as the "connecting end") must be electrically and mechanically secured to the pacemaker in a way that provides for a long-term safe and secure, yet detachable, connection. Those skilled in the pacemaker art have long sought for a simple, yet reliable and safe, technique for making this detachable electrical and mechanical connection between the pacemaker device and the connecting end of the pacemaker lead.

Figure 1:
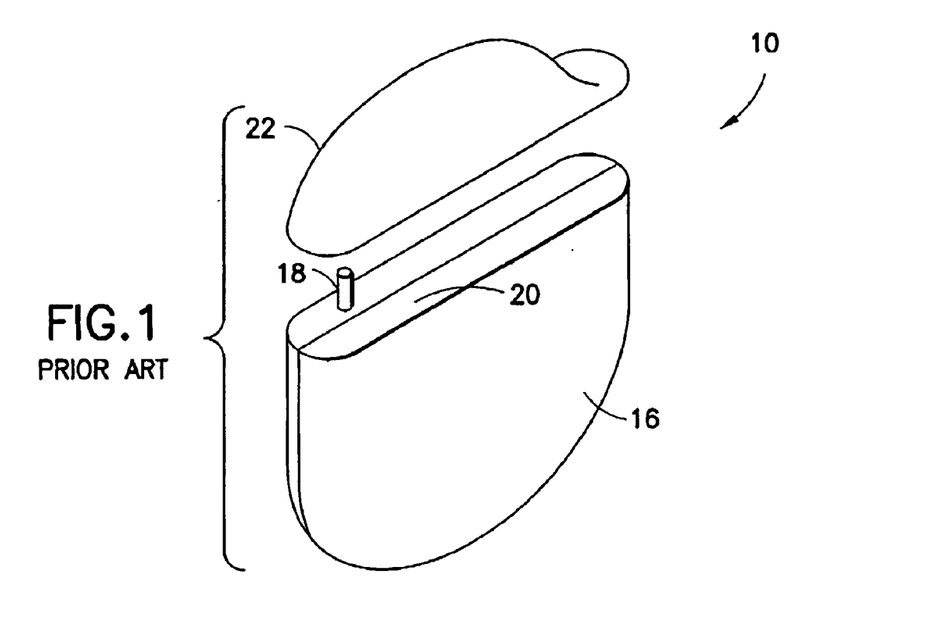
FIG. 1 is an exploded perspective view of a known pacemaker, illustrating a sealed pacemaker housing and its associated cast epoxy connector top.
Figure 2:
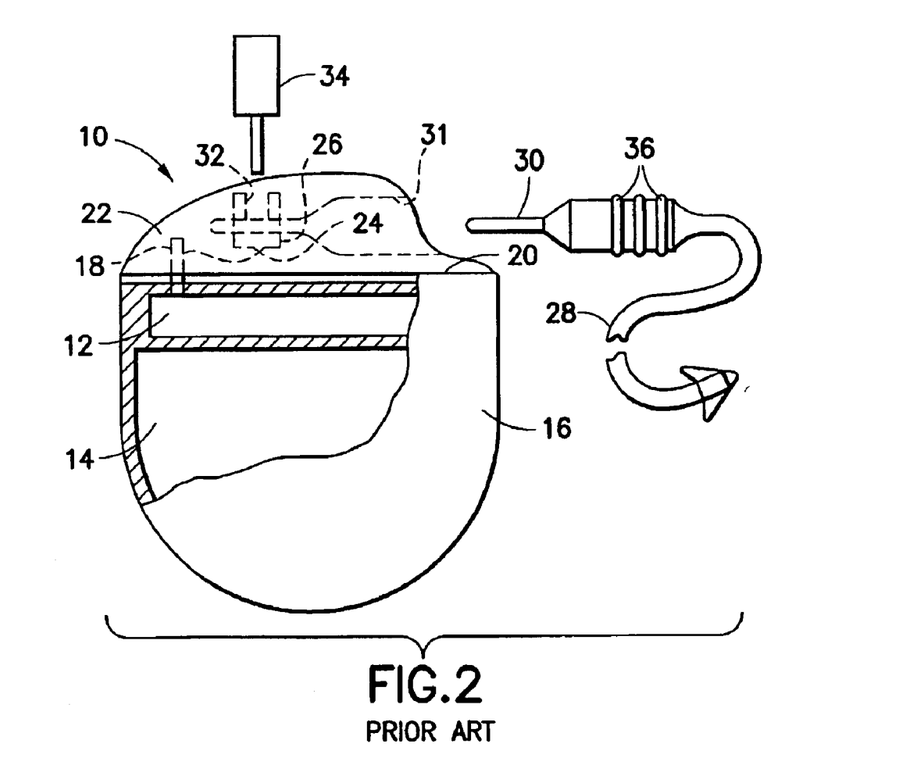
FIG. 2 is a side elevation view, partially cut away and in section, illustrating the assembled relationship between the pacemaker of FIG. 1 and its associated electrical pacemaker lead.

In order to appreciate the advantages of the present invention, it will help first to have a basic understanding of the manner in which the mechanical and electrical connection functions are carried out in known pacemakers. The main components associated with the connection function of known pacemakers are shown in FIGS. 1 and 2. A pacemaker 10 electrically includes a battery 14 that powers electrical circuits 12. The pacemaker electrical circuits 12 and battery 14 are mechanically housed and hermetically sealed in a suitable housing 16. Typically, this housing 16 is shaped to include a flat side or platform 20 to which a suitable epoxy connector 22 can be bonded. At least one feedthrough terminal 18, in electrical contact with the electrical circuits 12, passes through the housing 16 and protrudes out from the platform 20. This feedthrough terminal 18 is electrically isolated from the housing 16. A platinum wire 24, or other suitable conductive element, connects the terminal 18 to a conductive connector block 26 that is fitted within the connector 22. A pacemaker lead 28, having a proximal electrode 30, connects to the pacemaker electrical circuits by inserting the proximal electrode 30 into a receiving channel 31 of the connector 22 until the electrode 30 is in contact with the connector block 24. A set screw 32 is then securely tightened using a torque wrench 34 to firmly hold the electrode 30 in both mechanical and electrical connection with the connector block 26. A septum (not shown) is typically placed over the set screw 32 in order to prevent body fluids from seeping through the set screw hole. Further, sealing ribs or ridges 36 on the connecting end of the pacemaker lead are designed to tightly engage the inside edges of the receiving channel 31 in order to prevent any body fluids from entering into the receiving channel 31 once the connecting end of the lead has been pushed into the connector 22.

Representative descriptions of many of the features and functions of prior art pacemaker connection systems may be found in U.S. Pat. No. 4,934,366 to Truex et al., U.S. Pat. Nos. 5,012,807 and 5,076,270 to Stutz, Jr., U.S. Pat. No. 5,336,246 to Dantanarayana, U.S. Pat. No. 5,545,188 to Bradswhaw et al.,U.S. Pat. No. 5,899,930 to Flynn et al., and U.S. Pat. No. 6,029,089 to Hawkins et al. as well as to EPO publications EP 448,651 to Truex et al., EP 484,483 to Stutz, Jr. and EP 732,124 to Yee et al. While that which is described in these prior art references varies greatly relative to, for example, different types of locking mechanisms for performing the mechanical connection function, or different types of arrangements for performing the electrical feedthrough function, including the use of bipolar or multiple connector leads, all such systems include the use of a pre-molded or cast connector 22 that is bonded to a sealed pacemaker housing 16 in which the electrical circuits are located.

Historically, the pacemaker connector top has included epoxy resin which was cast over connector assemblies (for example, set screw connector blocks, garter spring connector blocks, and the like) which were fixtured in a pre-arranged shape. The use of the conductor ribbon set offered a significant improvement in holding the connector blocks together in the desired pre-arranged shape during the casting process and produced an attractive finished product.

However, the tooling and assembly methods used, and the curing process itself, is time and labor intensive. There are issues with flashing, wire breaks, damaged can, bubbles, exposed components and epoxy in the bores. These problems add significant rework time. Furthermore, epoxy connector tops are still prone to body fluid absorption and corrosion.

What is needed is an improved connector top that is easy to manufacture, reliable, and cost effective.

It was in light of the foregoing that the present invention was conceived and has now been reduced to practice.

SUMMARY OF THE INVENTION

A connector assembly includes a ring sub-assembly mounted on the housing of an implantable medical device with a passage for slidably receiving a proximal terminal of an electrical lead. The interior of the connector assembly is sealed when engaged with the electrical lead and has an annular shoulder in the passage facing away from the entrance. An electrical contact on the ring subassembly engages the electrical lead and an electrical conductor extends from that contact to exterior regions for electrical engagement with an external feed-through terminal of the housing. A tip sub-assembly having a tubular extremity extending to a terminal rim is fittingly received within the passage and extends to a terminal bore for slidably receiving a tip electrode of the electrical lead. An electrically conductive resilient member is received in the passage sandwiched between the annular shoulder and the terminal rim of the tubular extension and is electrically coupled to the electrical contact of the connector assembly. One example of such a resilient member is a garter spring coaxially received in the passage.

The present invention is directed towards an injection molded connector top for all IS-1 and IS-1 compatible connectors that would significantly reduce the above-mentioned problems. The design of the invention decreases the number of components (for example, to two injection molded sub-assemblies and two garter springs) which are then assembled and over cast in a final layer of epoxy. The complexity of the tooling and man-hours required to complete the final pacer is thereby significantly reduced. Additionally, the materials used are more immune to the absorption of body fluids and the new conductor assembly is not subject to corrosion.

A primary feature, then, of the present invention is the provision of an electrical connector used with an implantable medical device, such as a pacemaker, for connecting an implantable electrical lead to the electrical circuits within a hermetically sealed housing of the medical device.

Another feature of the present invention is the provision of such a connector for use with a sealed implantable pacemaker that combines the connector function with the feedthrough function and that eliminates the need for the cast or other preformed epoxy connector that has heretofore been used on implantable pacemakers.

Yet another feature of the present invention is the provision of such a connector which reduces the number of components required for its operation.

Still a further feature of the present invention is the provision of such a connector which requires fewer man-hours for its construction.

Yet a further feature of the present invention is the provision of such a connector with a reduced tendency to absorb body fluids.

Yet a still further feature of the present invention is the provision of such a connector which is crystal clear for easily viewing its interior, with improved reliability after assembly, and with improved corrosion resistance.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figures 3, 3A, 4:
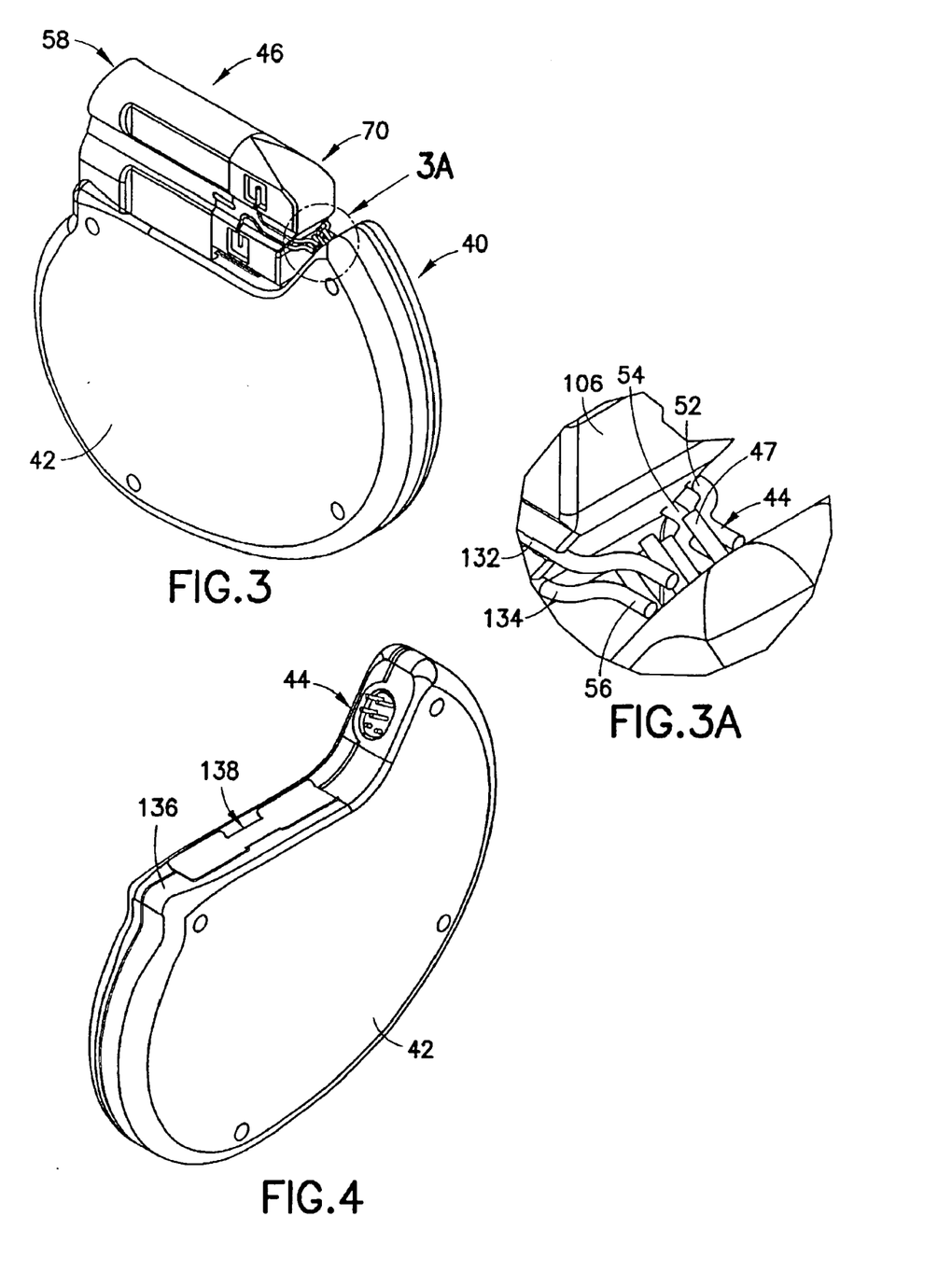
FIG. 3 is a perspective view of a pacemaker illustrating a connector assembly embodying the invention mounted on a sealed housing but before the application of an epoxy resin over-casting sealing the connector housing in place on the sealed housing.
FIG. 3A is a detail perspective view of a portion of the assembly illustrated in FIG. 3.
FIG. 4 is a perspective view of the sealed housing of the pacemaker of FIG. 3 ready to receive the connector housing of the invention.

Referring now to the drawings and, initially, to FIG. 3, an implantable medical device such as a pacemaker 40 includes an hermetically sealed housing 42 having electrical circuitry therein and including at least one insulated electrical feed-through member 44 coupled to the electrical circuitry and extending from the interior to the exterior of the housing, each feed-through member including an electrical terminal 47 (see FIGS. 3A and 4) carried externally of the housing. Although the present invention will be described with reference to the embodiments shown in the drawings, it should be understood that the present invention can be embodied in many alternate forms or embodiments. In addition, any suitable size, shape or type of elements or materials could be used.

Figure 5:
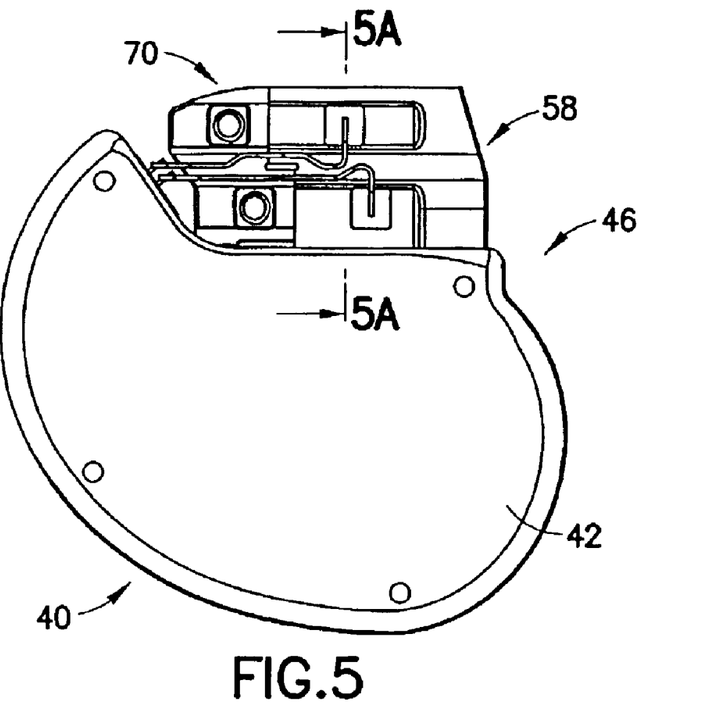
FIG. 5 is a side elevation view of a side of the pacemaker illustrated in FIG. 3, but showing the side opposite that shown in FIG. 3.
Figure 6:
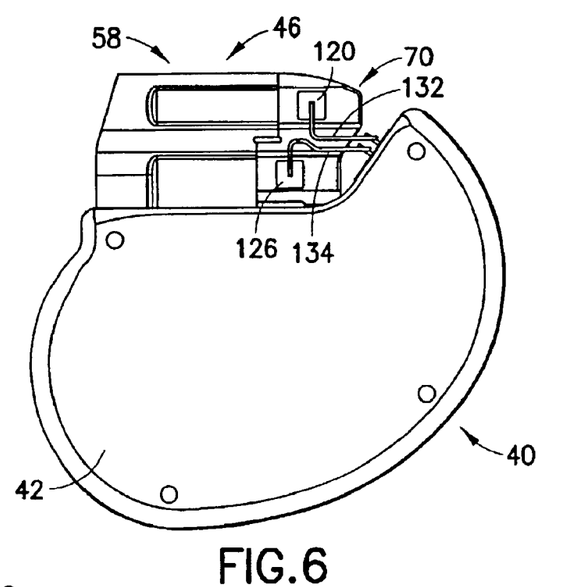
FIG. 6 is a side elevation view of the side of the pacemaker as illustrated in FIG. 3.
Figure 7:
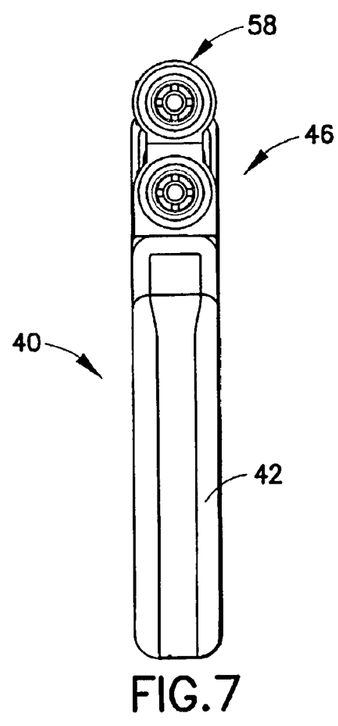
FIG. 7 is an end elevation view of the pacemaker illustrated in FIGS. 3, 5, and 6.
Figure 8:
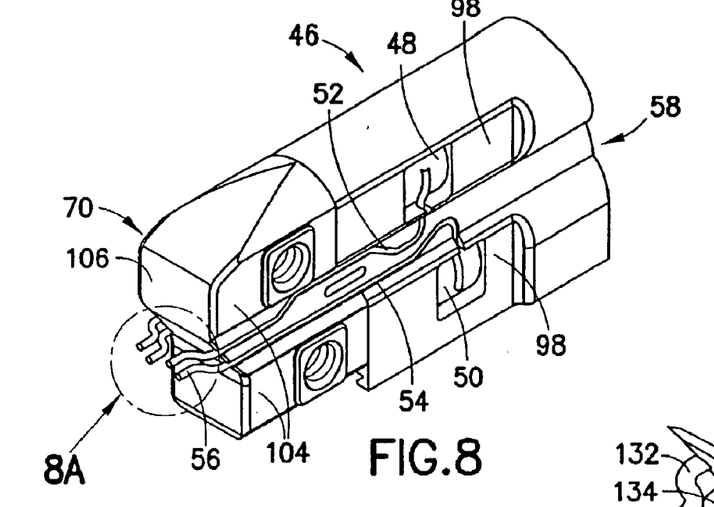
FIG. 8 is a detail perspective view of the connector assembly of the invention including the ring sub-assembly and the tip sub-assembly assembled together.
Figure 8A:
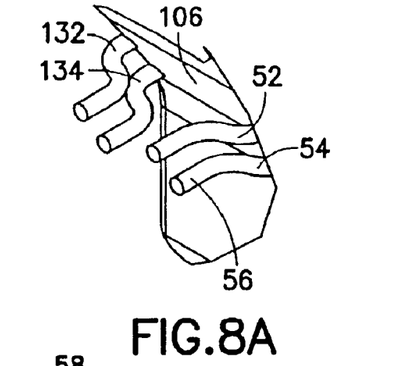
FIG. 8A is a detail perspective view of a portion of the assembly illustrated in FIG. 8.
Figure 9:
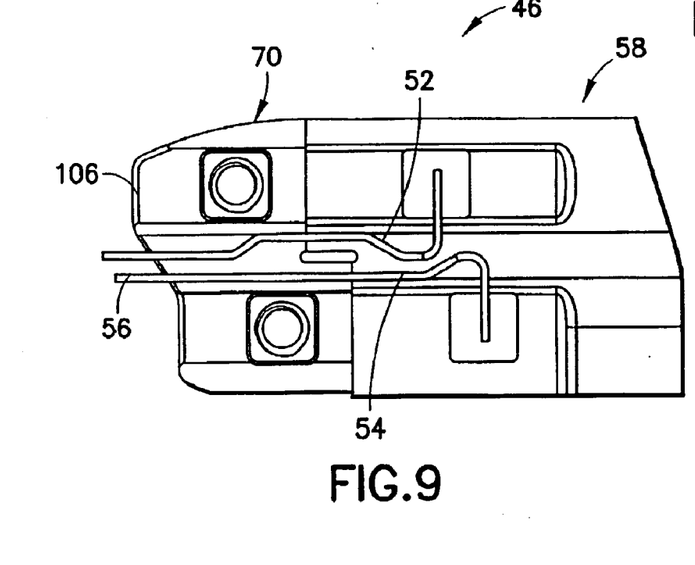
FIG. 9 is a side elevation view of the side of the connector assembly as illustrated in FIG. 8.
Figure 10:
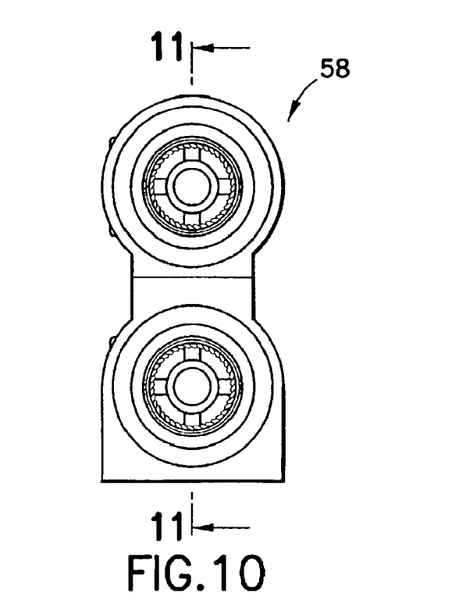
FIG. 10 is an end elevation view of the connector assembly illustrated in FIGS. 8 and 9.

With continued reference to FIG. 3 and with further reference now to FIGS. 5, 6, and 7, a connector assembly 46 is adapted to receive a proximal electrical-terminal-carrying end portion of an electrical lead, such as lead 28 of FIG. 2, in sealing engagement with the housing 42 such that the interior of the connector assembly is sealed from its exterior when so engaged with the electrical lead. Turning now also to FIGS. 8, 9, 10, and 11, the connector assembly 46 is seen to encompass a pair of electrical ring contacts 48, 50 which are adapted to be engaged by individual terminals of an electrical lead and the ring contacts have a pair of electrical conductors 52, 54 coupled, respectively, to them and extend from the interior to the exterior of the connector assembly. As best seen in FIG. 8A, each of the electrical conductors 52, 54 includes an electrical terminal 56 which is carried externally of the connector assembly. The connector assembly 46 is mounted on the sealed housing 42 in such a manner that the external terminal 56 of each electrical conductor 52, 54 on the connector assembly electrically contacts the external terminals 47 of the feed-through member 44 on the housing 42.

Turning now especially to FIGS. 11-14, the connector assembly 46 includes a ring sub-assembly 58 of molded, preferably injection molded, construction which has first and second entrances 60, 62 into first and second passages 64, 66, respectively, for slidably receiving first and second terminal ends, respectively, of the electrical lead (not shown), each of the passages having an annular shoulder 68 facing away from its associated entrance.

Now turning especially to FIGS. 16-19, the connector assembly 46 is also seen to include a Up sub-assembly 70 also of molded, preferably injection molded, construction which has first and second tubular extensions 72, 74 extending to first and second terminal rims 76, 78, respectively. The first and second terminal rims 76, 78 are fittingly received within the first and second passages 64, 66, respectively, of the ring sub-assembly 58. The first tubular extension 72 defines a first channel 80 extending to a first terminal bore 82 distant from the first terminal rim 76 for slidably receiving a tip electrode of the electrical lead. The second tubular extension 74 similarly defines a second channel 84 extending to a second terminal bore 86 distant from the second terminal rim 78, again for slidably receiving a tip electrode of the electrical lead.

Figure 11:
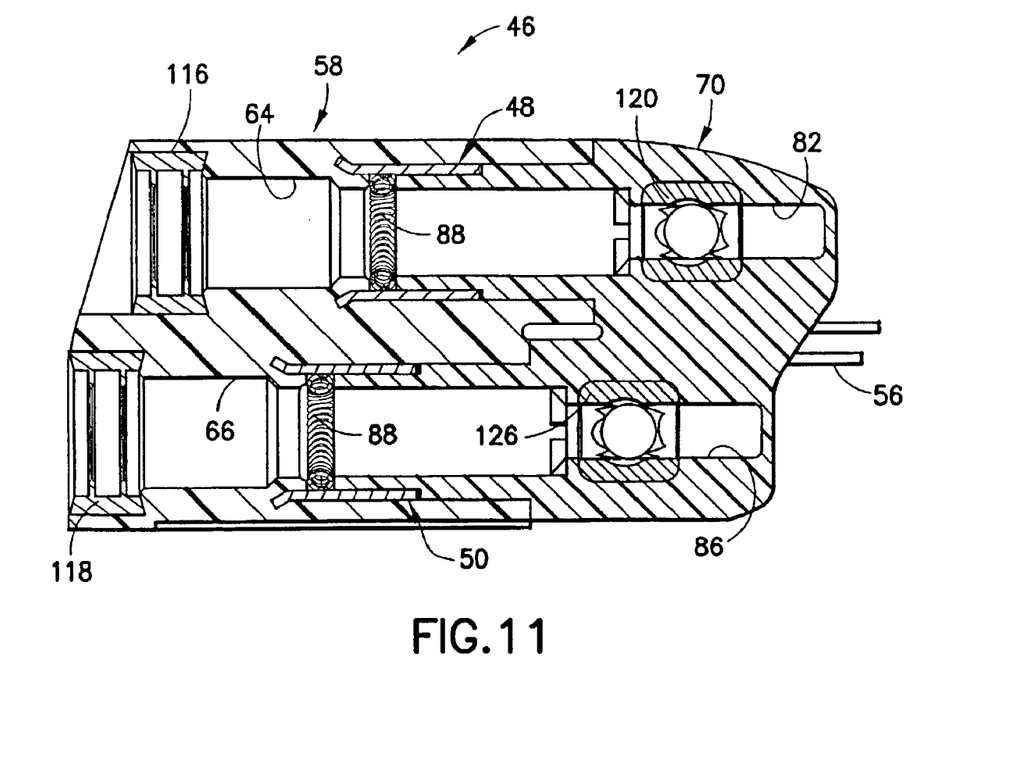
FIG. 11 is a cross-section view taken generally along line 11—11 in FIG. 10.

An electrically conductive resilient member 88 is received in each of the first and second passages 64, 66 of the ring sub-assembly 58 and engaged with the annular shoulder 68 of the ring sub-assembly, the terminal rims 76, 78 of the tubular extensions 72, 74 being engaged with an associated resilient member 88. A suitable form of resilient member for purposes of the invention is a garter spring, that is, a helical spring crafted into an annular configuration. As best seen in FIG. 11, each resilient member, or garter spring, 88 is electrically engaged to one of the ring contacts 48, 50 of the ring subassembly 58. Of course, the invention is intended to encompass a variety of other forms of electrically conductive resilient members capable of performing in a similar manner.

Figure 15:
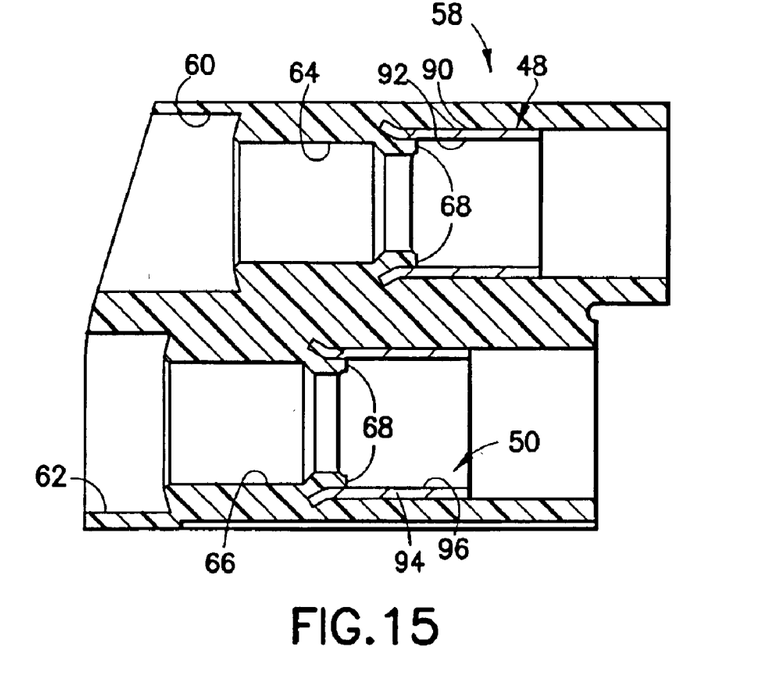
FIG. 15 is a cross section view taken generally along line 15—15 in FIG. 14.

Further, as best seen in FIGS. 11 and 15, a first of the ring contacts, namely ring contact 48, is generally cylindrical, fixed on the ring sub-assembly 58 in such a manner as to be coaxial with the first passage 64, and has an exterior surface 90 bonded to the ring sub-assembly and an interior surface 92 facing the first passage 64 and engaged with its associated garter spring 88. Similarly, a second of the ring contacts, namely ring contact 50, is generally cylindrical, is fixed on the ring subassembly 58 in such a manner as to be coaxial with the second passage 66, and has an exterior surface 94 bonded to the ring subassembly and an interior surface 96 facing the second passage 66 and engaged with its associated garter spring 88.

Figure 12:
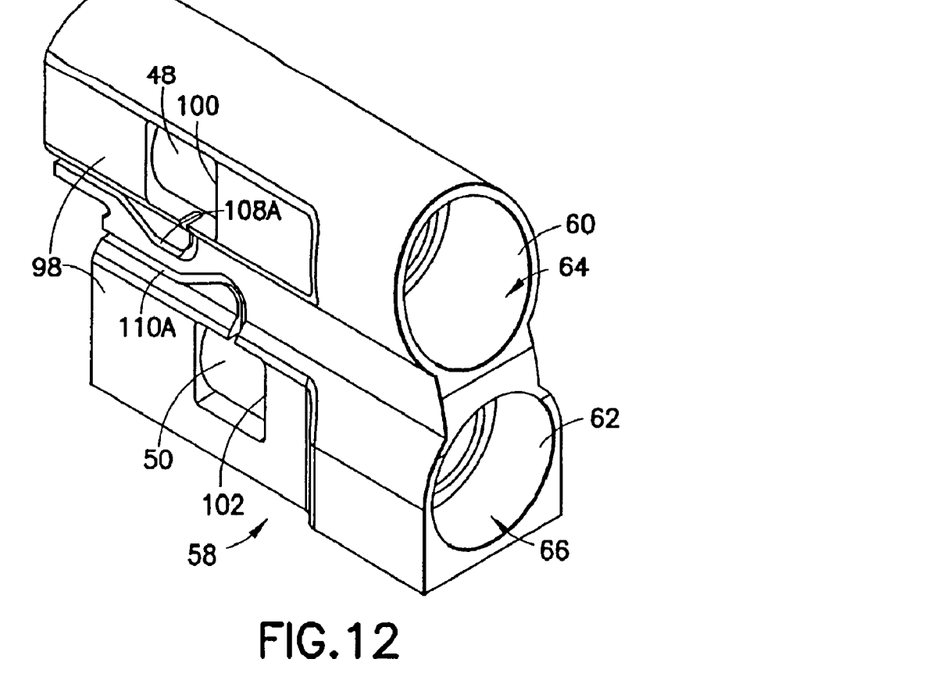
FIG. 12 is a perspective view of the ring sub-assembly of the invention.
Figure 13:
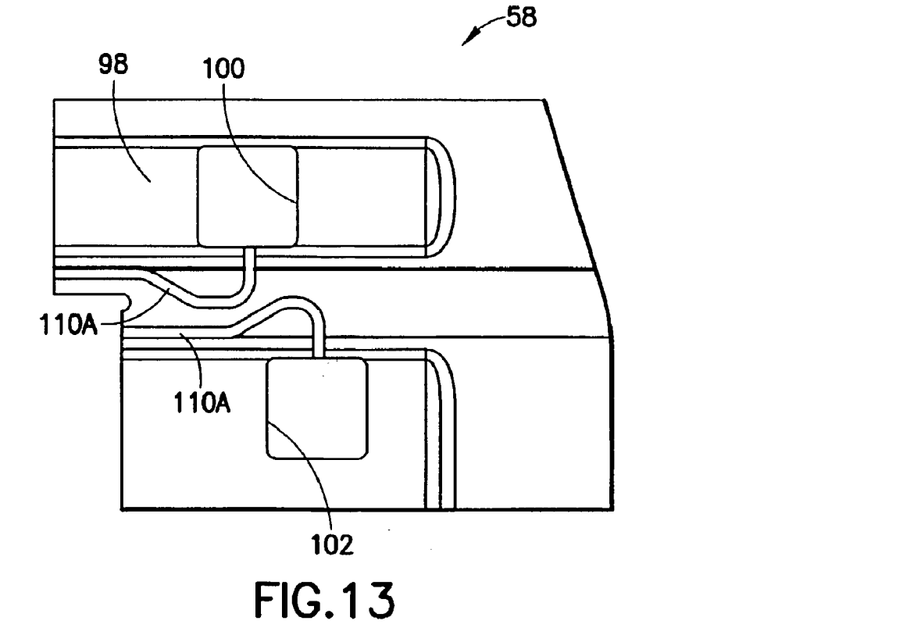
FIG. 13 is a side elevation view of the side of the ring subassembly as illustrated in FIG. 12.
Figure 14:
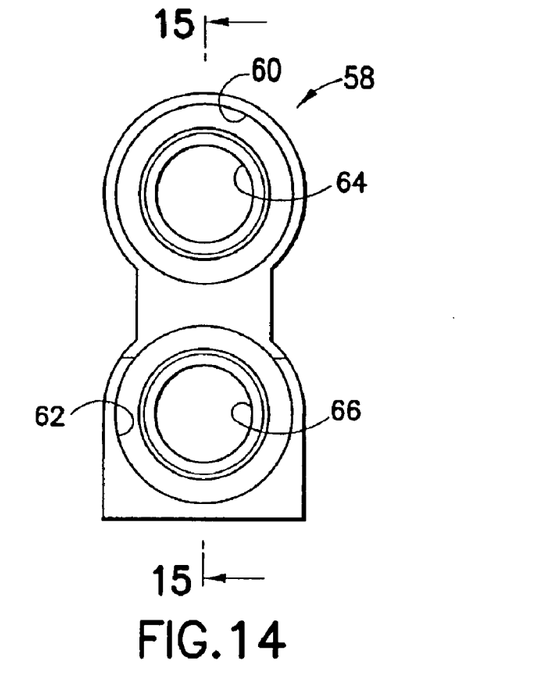
FIG. 14 is an end elevation view of the ring subassembly illustrated in FIGS. 12 and 13.

Viewing especially FIGS. 12 and 13, the ring subassembly 58 is seen to have a side wall 98 with a first opening 100 coextensive with the first ring contact 48 and a second opening 102 coextensive with the second ring contact 50. Then, viewing especially FIGS. 16 and 17, the tip sub-assembly 70 is seen to have a side wall 70 generally coplanar with the side wall 98 of the ring sub-assembly 58 (especially viewing FIG. 8) and an end wall 70 distant from the terminal rims 76, 78. The first longitudinally extending conductor 52 is mounted on the side wall 98 of the ring sub-assembly 58 and on the side wall of the tip sub-assembly 70 and extends from a distal end electrically connected in a suitable fashion to the first ring contact 48 to an electrical terminal 56 at a proximal end adjacent the end wall 106 where it is electrically connected in a suitable fashion to the electrical terminal 47 associated with one of the feedthrough members 44. In a similar manner, the second longitudinally extending conductor 54 is also mounted on the side wall 98 of the ring sub-assembly 58 and on the side wall of the tip sub-assembly 70 and extends from a distal end electrically connected in a suitable fashion to the second ring contact 50 to an electrical terminal 56 at a proximal end adjacent the end wall 106 where it is electrically connected in a suitable fashion to the electrical terminal 47 associated with one of the feed-through members 44. This manner of electrically joining the terminals 56 to the terminals 47 is generally illustrated in FIG. 3A.

Figure 7A:
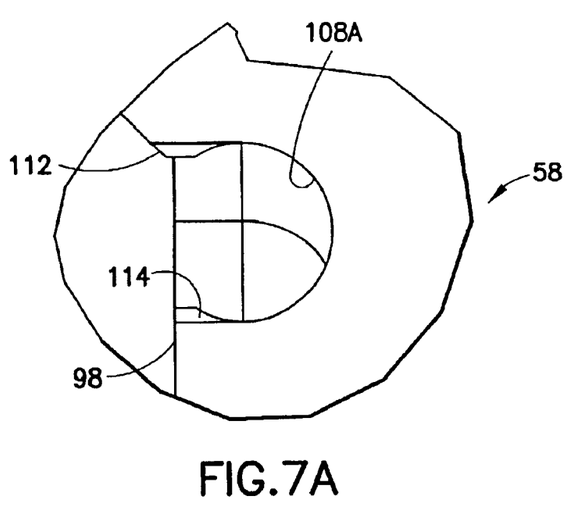
FIG. 7A is a detail end elevation illustrating a small portion of FIG. 7.
Figure 16:
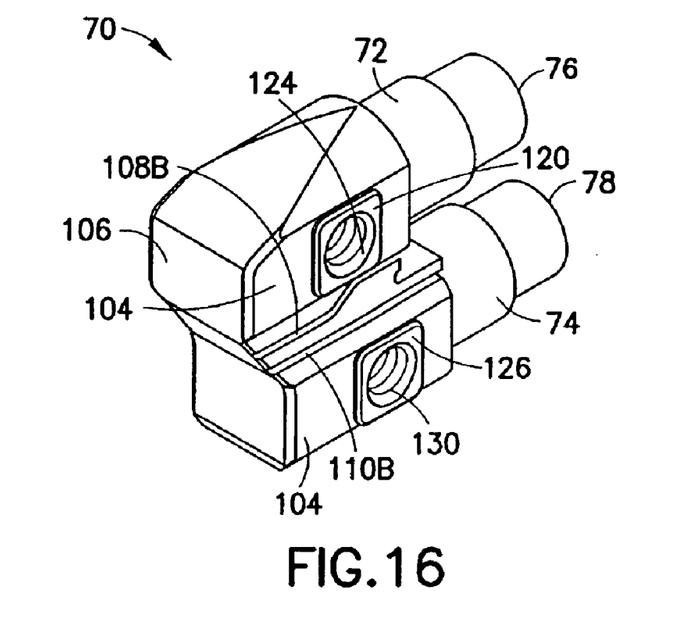
FIG. 16 is a perspective view of the tip sub-assembly of the invention.
Figure 17:
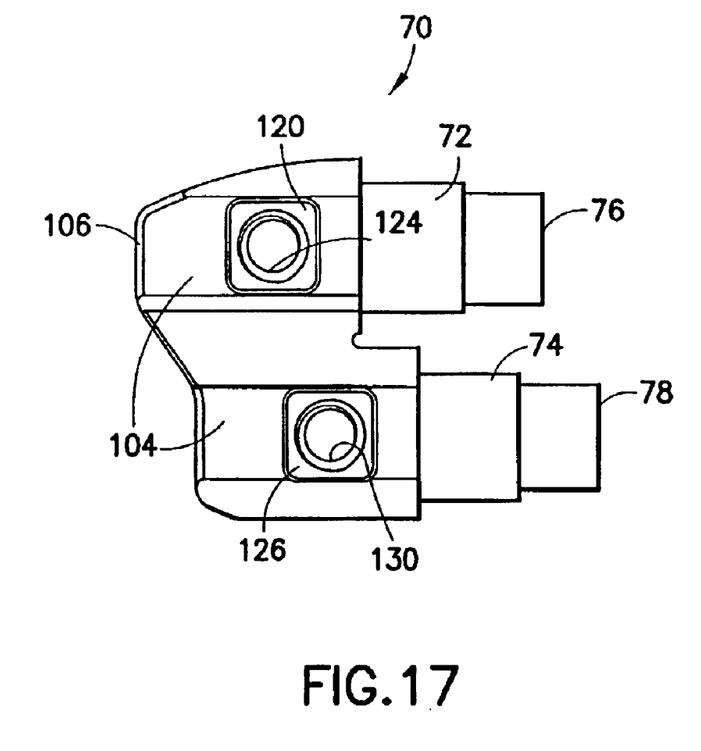
FIG. 17 is a side elevation view of the side of the tip subassembly as illustrated in FIG. 16.
Figure 18:
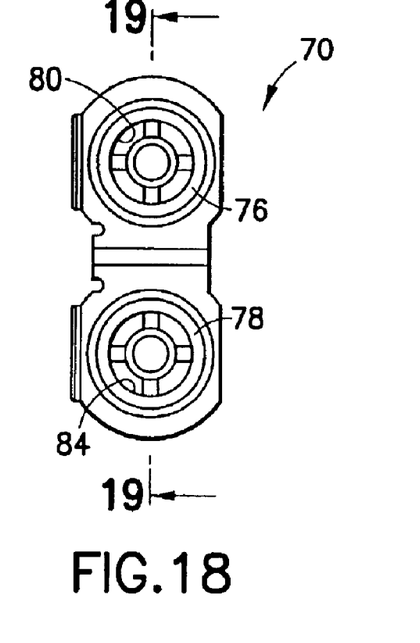
FIG. 18 is an end elevation view of the ring sub-assembly illustrated in FIGS. 16 and 17.

As seen especially well in FIGS. 7A, 12, and 16, the side wall 98 of the ring sub-assembly 58 and the side wall 104 of the tip sub-assembly 70 have aligned, communicating longitudinally extending first and second grooves 108A, 108B, and 110A, 110B, respectively, for fittingly receiving the first and second longitudinally extending conductors 52, 54, respectively. As seen in FIG. 7A, locking tabs 112, 114 are formed at the intersection of the groove 108A and the side wall 98 for fittingly engaging the longitudinally extending conductor 52 and firmly retaining it in the groove 108A. This construction is repeated at the groove 108B of the tip sub-assembly 70 for the conductor 52 as it is in the grooves 110A and 110B of both the ring sub-assembly 58 and the tip sub-assembly 70 for the conductor 54.

To assure that the interior of the connector assembly 46 is isolated from body fluids when implanted, first and second annular seals 116, 118 are suitably fixed to the ring sub-assembly at the entrances 60, 62, respectively, to the passages 64, 66.

Figure 19:
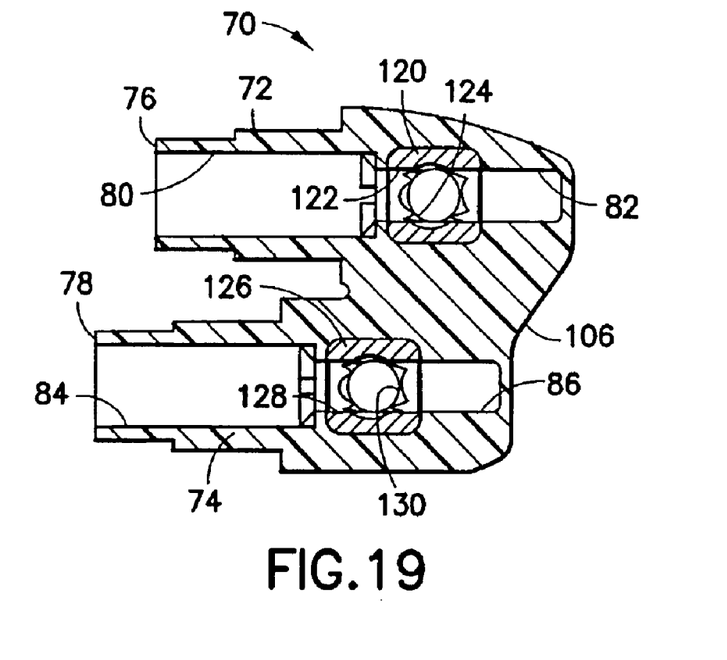
FIG. 19 is a cross section view taken generally along line 19—19 in FIG. 18.
Figure 20:
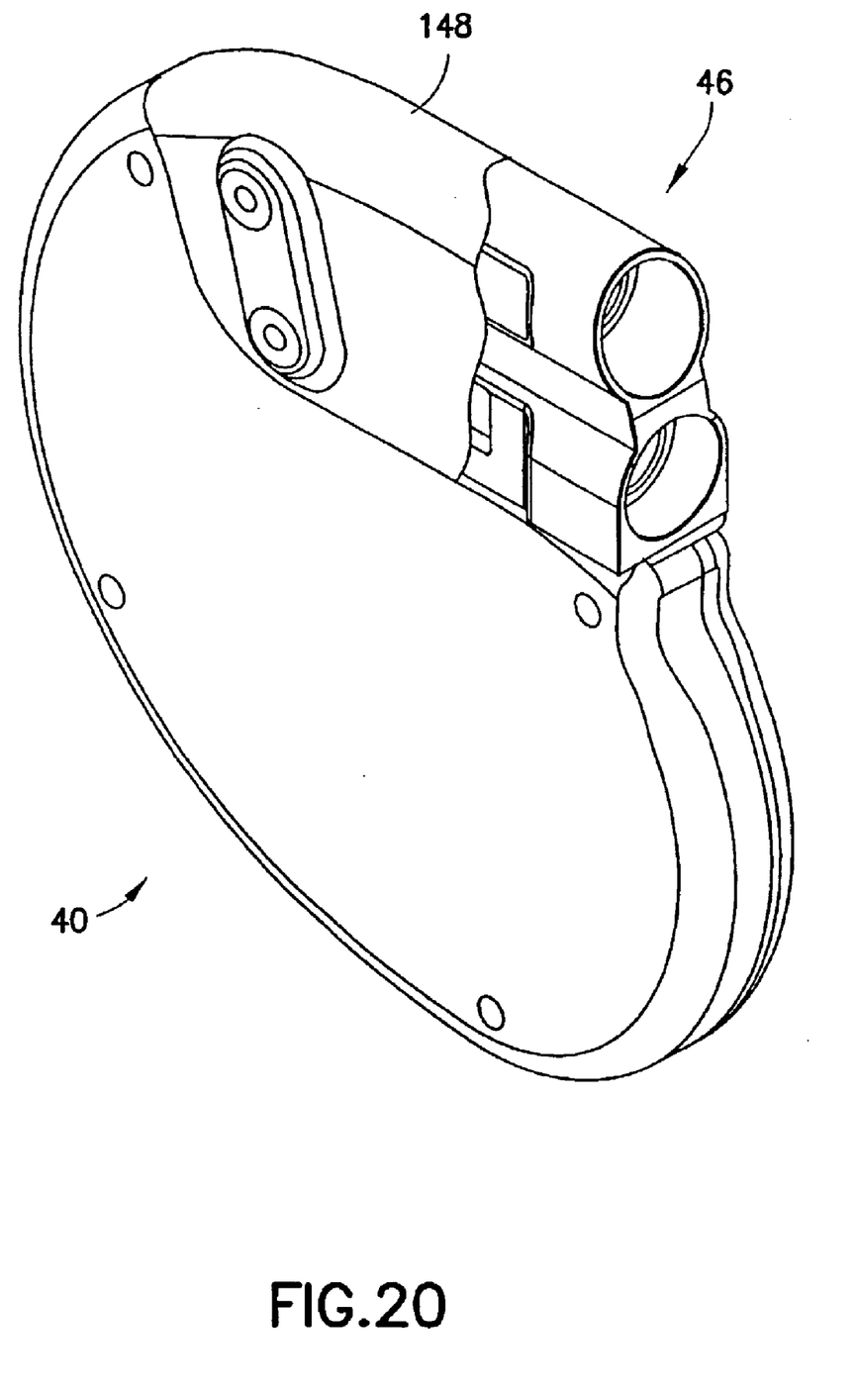
FIG. 20 is a perspective view of a pacemaker embodying the invention illustrating the connector assembly and the connections to the feed-through member of the sealed housing encapsulated in an epoxy resin over-casting.

Viewing especially FIGS. 11 and 19, the tip sub-assembly 70 includes a first connector block 120 mounted in the region of the first terminal bore 82. The connector block has a central bore 122 coaxial with the terminal bore 82 and is also formed with a transverse tapped aperture 124. A second connector block 126 is similarly mounted in the tip subassembly 70, projects through the side wall 104 (FIG. 16), and has a central bore 128 coaxial with the second terminal bore and is also formed with a transverse tapped aperture 130. A first longitudinally extending conductor 132 is mounted on the side wall 104 of the tip sub-assembly 70 in a manner similar to the mounting of the conductors 52, 54 which occurs on an opposite side of the tip sub-assembly. The conductor 132 extends from a distal end electrically connected to the connector block 120 to a proximal end adjacent the end wall 106 electrically connected to an electrical terminal associated with one of the feed-through members 44 (see FIGS. 3, 3A, and 6).

In a similar manner, a second longitudinally extending conductor 134 is mounted on the side wall 104 of the tip sub-assembly 70 and extends from a distal end electrically connected to the second connector block 126 to a proximal end adjacent the end wall 106 electrically connected to an electrical terminal associated with another one of the feed-through members 44.

The conductors 132, 134 are firmly held in place on the side wall 104 of the tip sub-assembly by means of associated grooves similar to grooves 110A, 110B and by associated locking tabs similar to locking tabs 112, 114.

Figure 5A:
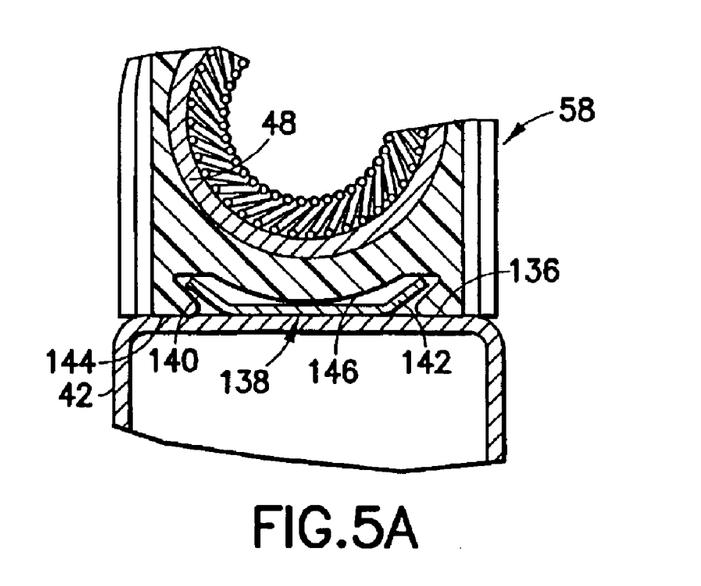
FIG. 5A is a cross-section view taken generally along line 5A—5A in FIG. 5.

Turning now to FIGS. 4, 5, and 5A, it is seen that the sealed housing 42 has an upper planar surface 136 upon which is suitably fixedly mounted a longitudinally extending connector brace 138 having a central bight portion 139 and opposed angularly upstanding flange members 140, 142 extending lengthwise of the connector brace. The ring sub-assembly 58 has an underside 144 formed with a longitudinally extending cavity 146 for slidable engagement with the connector brace 138 for placement of the connector assembly on the sealed housing. The cavity 146 and connector brace 138 coact to properly position the connector assembly 46 on the surface 136 of the sealed housing 42, preventing lateral movement of the connector housing relative to the sealed housing. When the electrical conductors 52, 54, 132, 134 are joined, as by welding, to the electrical terminal 47, the connector housing is thereby also prevented from moving longitudinally relative to the sealed housing. When this construction is achieved, the connector assembly 46 and the connections to the feed-through member 44 are then encapsulated in an epoxy resin over-casting 148 which totally seals the connector assembly and all of its associated components onto the sealed housing 42. See FIG. 19.

It should be understood that the foregoing description is only illustrative of the invention. Various alternatives and modifications can be devised by those skilled in the art without departing from the invention. For example, although the connector assembly 46 has been described and illustrated as having a pair of entrances and passages for receiving a pair of electrical contacts for an electrical lead which extends into the heart, the connector assembly may actually be constructed to only receive one contact from the electrical lead or a plurality of contacts from that lead. Accordingly, the present invention is intended to embrace all such alternatives, modifications and variances which fall within the scope of the appended claims.

What is claimed is:

1. An implantable medical device comprising:
   an hermetically sealed housing having electrical circuitry therein and comprising at least one insulated electrical feed-through member coupled to the electrical circuitry and extending from the interior to the exterior of the housing, the feed-through member comprising an electrical terminal carried externally of the housing;
   a connector assembly adapted to receive a proximal electrical-terminal-carrying end portion of an electrical lead in sealing engagement with the housing whereby the interior of the connector assembly is sealed from the exterior thereof when in engagement with the electrical lead, the connector assembly having a pair of electrical contacts therein adapted to be engaged by individual terminals of the electrical lead and having at least a pair of electrical conductors coupled, respectively, to the contacts and extending from the interior of the connector assembly to the exterior of the connector assembly, the electrical conductors each comprising an electrical terminal carried externally of the connector assembly; and
   the connector assembly mounted on the sealed housing in such a manner that the external terminal of each electrical conductor on the connector assembly electrically contacts the external terminal of the feed-through member on the housing, the connector assembly comprising:
   a ring sub-assembly having first and second entrances into first and second passages, respectively, for slidably receiving first and second terminal ends, respectively, of the electrical lead, each of the passages having an annular shoulder facing away from its associated entrance; and
   a tip sub-assembly having first and second tubular extensions extending to first and second terminal rims, respectively, fittingly received within the first and second passages, respectively, of the ring sub-assembly, the first tubular extension defining a first channel extending to a first terminal bore distant from the first terminal rim for slidably receiving a tip electrode of the electrical lead, the second tubular extension defining a second channel extending to a second terminal bore distant from the second terminal rim for slidably receiving a tip electrode of the electrical lead; and
   an electrically conductive resilient member received in each of the first and second passages and engaged with the annular shoulder therein, the terminal rim of each tubular extension being engaged with an associated resilient member, each resilient member being electrically coupled to one of the electrical contacts of the connector assembly.

2. An implantable medical device as set forth in claim 1: wherein the ring sub-assembly and the tip sub-assembly are both of molded construction.

3. An implantable medical device as set forth in claim 1: wherein the ring sub-assembly and the tip sub-assembly are both of injection molded construction.

4. An implantable medical device as set forth in claim 1: wherein the electrically conductive resilient member comprises a garter spring coaxially received in each of the first and second passages.

5. An implantable medical device as set forth in claim 1: wherein the pair of electrical contacts comprises:
   a first ring contact fixed on the ring sub-assembly coaxial with the first passage and having an exterior surface bonded to the ring sub-assembly and an interior surface facing the first passage and engaged with the resilient member; and
   a second ring contact fixed on the ring sub-assembly coaxial with the second passage and having an exterior surface bonded to the ring sub-assembly and an interior surface facing the second passage and engaged with the resilient member.

6. An implantable medical device as set forth in claim 5: wherein the ring sub-assembly has a side wall with a first opening coextensive with the first ring contact and a second opening coextensive with the second ring contact;
   wherein the tip sub-assembly has a side wall generally coplanar with the side wall of the ring sub-assembly and an end wall distant from the terminal rim; and
   comprising:
   a first longitudinally extending conductor mounted on the side wall and extending from a distal end electrically connected to the first ring contact to a proximal end adjacent the end wall electrically connected to an electrical terminal associated with one of the feed-through members; and a second longitudinally extending conductor mounted on the side wall and extending from a distal end electrically connected to the second ring contact to a proximal end adjacent the end wall electrically connected to an electrical terminal associated with another one of the feed-through members.

7. An implantable medical device as set forth in claim 6:
wherein the side wall of the ring sub-assembly and the side wall of the tip sub-assembly have aligned, communicating longitudinally extending first and second grooves for fittingly receiving the first and second longitudinally extending conductors, respectively.

8. An implantable medical device as set forth in claim 7 further comprising locking tabs at the intersection of the grooves and the side walls for fittingly engaging the first and second longitudinally extending conductors and firmly retaining the conductors in their respective first and second grooves.

9. An implantable medical device as set forth in claim 1 further comprising:
first and second annular seals fixed to the ring subassembly at the entrance, respectively, to the first and second passages thereof.

10. An implantable medical device as set forth in claim 1:
wherein the tip sub-assembly has a side wall; and further comprising:
a first connector block mounted in the tip sub-assembly and having a central bore coaxial with the first terminal bore and having a transverse tapped aperture therein; and
a second connector block mounted in the tip sub-assembly and having a central bore coaxial with the first terminal bore and having a transverse tapped aperture therein; and
a first longitudinally extending conductor mounted on the side wall of the tip sub-assembly and extending from a distal end electrically connected to the first connector block to a proximal end adjacent the end wall electrically connected to an electrical terminal associated with one of the feed-through members; and
a second longitudinally extending conductor mounted on the side wall of the tip subassembly and extending from a distal end electrically connected to the second connector block to a proximal end adjacent the end wall electrically connected to an electrical terminal associated with another one of the feed-through members.

11. An implantable medical device as set forth in claim 10:
wherein the side wall of the Up sub-assembly has longitudinally extending first and second grooves for fittingly receiving the first and second longitudinally extending conductors, respectively.

12. An implantable medical device as set forth in claim 11 further comprising locking tabs at the intersection of the grooves and the side wall for fittingly engaging the first and second longitudinally extending conductors and firmly retaining the conductors in their respective first and second grooves.

13. An implantable medical device as set forth in claim 5:
wherein the ring sub-assembly has a side wall with a first opening coextensive with the first ring contact and a second opening coextensive with the second ring contact;
wherein the tip sub-assembly has an end wall distant from the terminal rim; and comprising:
a first longitudinally extending conductor mounted on the side wall and extending from a distal end electrically connected to the first ring contact to a proximal end adjacent the end wall electrically connected to an electrical terminal associated with one of the feed-through members; and
a second longitudinally extending conductor mounted on the side wall and extending from a distal end electrically connected to the second ring contact to a proximal end adjacent the end wall electrically connected to an electrical terminal associated with another one of the feed-through members; and
wherein the tip sub-assembly has a side wall; and further comprising:
a first connector block mounted in the tip sub-assembly and having a central bore coaxial with the first terminal bore and having a transverse tapped aperture therein; and
a second connector block mounted in the tip sub-assembly and having a central bore coaxial with the first terminal bore and having a transverse tapped aperture therein; and
a first longitudinally extending conductor mounted on the side wall of the tip sub-assembly and-extending from a distal end electrically connected to the first connector block to a proximal end adjacent the end wall electrically connected to an electrical terminal associated with one of the feed-through members; and
a second longitudinally extending conductor mounted on the side wall of the tip sub-assembly and extending from a distal end electrically connected to the second connector block to a proximal end adjacent the end wall electrically connected to an electrical terminal associated with another one of the feed-through members.

14. An implantable medical device as set forth in claim 13:
wherein the sealed housing has an upper planar surface;
wherein a longitudinally extending connector brace having a central bight portion contiguous with the upper planar surface is mounted on the sealed housing, the connector brace comprising opposed angularly upstanding flange members extending lengthwise of the connector brace; and
wherein the ring subassembly has an underside formed with a longitudinally extending cavity for slidable engagement with the connector brace for placement of the connector assembly on the sealed housing.

15. An implantable medical device comprising:
an hermetically sealed housing having electrical circuitry therein and comprising at least one insulated electrical feedthrough member coupled to the electrical circuitry and extending from the interior to the exterior of the housing, the feed-through member comprising an electrical terminal carried externally of the housing;
a connector assembly adapted to receive a proximal electrical-terminal-carrying end portion of an electrical lead in sealing engagement with the housing whereby the interior of the connector assembly is sealed from the exterior thereof when in engagement with the electrical lead, the connector assembly having an electrical contact therein adapted to be engaged by a terminal of the electrical lead and having an electrical conductor coupled to the contact and extending from the interior of the connector assembly to the exterior of the connector assembly, the electrical conductor comprising an electrical terminal carried externally of the connector assembly, and the connector assembly mounted on the sealed housing in such a manner that the external terminal of the electrical conductor on the connector assembly electrically contacts the external terminal of the feed-through member on the housing, the connector assembly comprising:

a ring sub-assembly having an entrance into a passage for slidably receiving a terminal end of the electrical lead having an annular shoulder facing away from the entrance; and a tip sub-assembly having a tubular extremity extending to a terminal rim fittingly received within the passage of the ring sub-assembly, the tubular extension defining a channel extending to a terminal bore distant from the terminal rim for slidably receiving a tip electrode of the electrical lead; and an electrically conductive resilient member received in the passage and engaged with the annular shoulder therein, the terminal rim of the tubular extension being engaged with the resilient member, the resilient member being electrically coupled to the electrical contact of the connector assembly.

16. An implantable medical device as set forth in claim 15:

wherein the ring sub-assembly and the tip sub-assembly are both of molded construction.

17. An implantable medical device as set forth in claim 15:

wherein the ring sub-assembly and the tip sub-assembly are both of injection molded construction.

18. An implantable medical device as set forth in claim 15:

wherein the electrically conductive resilient member comprises a garter spring coaxially received in each of the first and second passages.

19. An implantable medical device as set forth in claim 15: wherein the electrical contact comprises:

a ring contact fixed on the ring sub-assembly coaxial with the passage and having an exterior surface bonded to the ring sub-assembly and an interior surface facing the passage and engaged with the resilient member.

20. An implantable medical device as set forth in claim 19:

wherein the ring sub-assembly has a side wall with an opening coextensive with the ring contact;

wherein the tip sub-assembly has a side wall generally coplanar with the side wall of the ring sub-assembly and an end wall distant from the terminal rim; and further comprising:

a longitudinally extending conductor mounted on the side wall and extending from a distal end electrically connected to the ring contact to a proximal end adjacent the end wall electrically connected to an electrical terminal associated with one of the feed-through members.

21. An implantable medical device as set forth in claim 20:

wherein the side wall of the ring sub-assembly and the side wall of the tip sub-assembly have aligned, communicating longitudinally extending grooves for fittingly receiving the longitudinally extending conductor.

22. An implantable medical device as set forth in claim 21 further comprising locking tabs at the intersection of the grooves and the side walls for fittingly engaging the longitudinally extending conductor and firmly retaining the conductor in the grooves.

23. An implantable medical device as set forth in claim 15 further comprising:

an annular seal fixed to the ring sub-assembly at the entrance to the passage thereof.

24. An implantable medical device as set forth in claim 15:

wherein the tip sub-assembly has a side wall; and further comprising:

a connector block mounted in the tip sub-assembly and having a central bore coaxial with the terminal bore and having a transverse tapped aperture therein; and a longitudinally extending conductor mounted on the side wall of the tip sub-assembly and extending from a distal end electrically connected to the connector block to a proximal end adjacent the end wall electrically connected to an electrical terminal associated with one of the feed-through members.

25. An implantable medical device as set forth in claim 24:

wherein the side wall of the tip sub-assembly has a longitudinally extending groove for fittingly receiving the longitudinally extending conductor.

26. An implantable medical device as set forth in claim 25 further comprising locking tabs at the intersection of the groove and the side wall for fittingly engaging the longitudinally extending conductor and firmly retaining the conductor in the groove.

27. A connector assembly for use with an implantable medical device, the connector assembly comprising:

a ring sub-assembly mounted on the hermetically sealed housing of the medical device and having an entrance into a passage for slidably receiving a proximal electrical-terminal-carrying end portion of an electrical lead in sealing engagement with the sealed housing containing electrical circuitry with at least one insulated electrical feed-through member coupled to the electrical circuitry and extending from the interior to the exterior of the housing, the feed-through member comprising an electrical terminal carried externally of the housing, whereby the interior of the connector assembly is sealed from the exterior thereof when in engagement with the electrical lead and having an annular shoulder facing away from the entrance;

an electrical contact on the ring sub-assembly adapted to be engaged by a terminal of the electrical lead;

an electrical conductor coupled to the contact and extending from the interior of the connector assembly to the exterior of the connector assembly comprising an electrical terminal carried externally of the connector assembly for electrical engagement with the external electrical terminal of the feed-through member of the sealed housing;

a tip sub-assembly having a tubular extremity extending to a terminal rim fittingly received within the passage of the ring sub-assembly, the tubular extension defining a channel extending to a terminal bore distant from the terminal rim for slidably receiving a tip electrode of the electrical lead; and an electrically conductive resilient member received in the passage and engaged with the annular shoulder therein, the terminal rim of the tubular extension being engaged with the resilient member, the resilient member being electrically coupled to the electrical contact of the connector assembly.

28. A connector assembly as set forth in claim 27;
wherein the ring sub-assembly and the Up sub-assembly are both of molded construction.

29. A connector assembly as set forth in claim 27:
wherein the ring sub-assembly and the Up sub-assembly are both of injection molded construction.

30. An implantable medical device as set forth in claim 27:
wherein the electrically conductive resilient member comprises a garter spring coaxially received in each of the first and second passages.

31. A connector assembly as set forth in claim 27:
wherein the electrical contact comprises:
a ring contact fixed on the ring sub-assembly coaxial with the passage and having an exterior surface bonded to the ring subassembly and an interior surface facing the passage and engaged with the resilient member.

32. A connector assembly as set forth in claim 31:
wherein the ring subassembly has a side wall with an opening coextensive with the ring contact;
wherein the tip sub-assembly has a side wall generally coplanar with the side wall of the ring sub-assembly and an end wall distant from the terminal rim; and
further comprising:
a longitudinally extending conductor mounted on the side wall and extending from a distal end electrically connected to the ring contact to a proximal end adjacent the end wall electrically connected to an electrical terminal associated with one of the feedthrough members.

33. An implantable medical device as set forth in claim 32:
wherein the side wall of the ring sub-assembly and the side wall of the tip sub-assembly have aligned, communicating longitudinally extending grooves for fittingly receiving the longitudinally extending conductor.

34. An implantable medical device as set forth in claim 33 further comprising locking tabs at the intersection of the grooves and the side walls for fittingly engaging the first and second longitudinally extending conductors and firmly retaining the conductors in their respective first and second grooves.

35. A connector assembly as set forth in claim 27 further comprising:
first and second annular seals fixed to the ring subassembly at the entrance to the passage thereof.

36. A connector assembly as set forth in claim 27:
wherein the tip sub-assembly has a side wall; and further comprising:
a connector block mounted in the tip sub-assembly and having a central bore coaxial with the terminal bore and having a transverse tapped aperture therein; and
a longitudinally extending conductor mounted on the side wall of the tip sub-assembly and extending from a distal end electrically connected to the connector block to a proximal end adjacent the end wall electrically connected to an electrical terminal associated with one of the feed-through members.

37. An implantable medical device as set forth in claim 36:
wherein the side wall of the tip sub-assembly has longitudinally extending first and second grooves for fittingly receiving the first and second longitudinally extending conductors, respectively.

38. An implantable medical device as set forth in claim 37 further comprising locking tabs at the intersection of the grooves and the side wall for fittingly engaging the first and second longitudinally extending conductors and firmly retaining the conductors in their respective first and second grooves.

* * * * *